(12) United States Patent
Lu

(10) Patent No.: US 6,283,118 B1
(45) Date of Patent: Sep. 4, 2001

(54) ULTRASONIC NEBULIZER

(76) Inventor: Hsueh-Yu Lu, 5F-23, 70, Fu-Hsing Road, Taoyuan (TW)

( * ) Notice: Subject to any disclaimer, the term of this patent is extended or adjusted under 35 U.S.C. 154(b) by 0 days.

(21) Appl. No.: 09/416,750

(22) Filed: Oct. 13, 1999

(51) Int. Cl.$^7$ ............................................. A61M 11/00
(52) U.S. Cl. ............................ 128/200.16; 128/200.18
(58) Field of Search .................. 128/200.14, 200.16, 128/200.18; 239/102.1, 102.2, 338

(56) References Cited

U.S. PATENT DOCUMENTS

| | | | | |
|---|---|---|---|---|
| 1,035,049 | * | 8/1912 | Engstrom et al. | 128/200.18 |
| 3,291,122 | * | 12/1966 | Engstrom et al. | 128/200.16 |
| 3,561,444 | * | 2/1971 | Boucher | 128/200.16 |
| 3,690,317 | * | 9/1972 | Millman | 128/200.16 |
| 3,746,000 | * | 7/1973 | Edwards | 128/200.16 |
| 3,901,443 | * | 8/1975 | Mitsui et al. | 239/102 |
| 4,001,650 | * | 1/1977 | Romain | 128/200.16 |
| 4,976,259 | * | 12/1990 | Higson et al. | 128/200.18 |
| 5,511,539 | * | 4/1996 | Lien | 128/200.16 |
| 5,865,171 | * | 2/1999 | Cinquin | 128/200.16 |
| 5,921,232 | * | 7/1999 | Yokoi et al. | 128/200.16 |
| 6,152,383 | * | 11/2000 | Chen | 128/200.16 |

FOREIGN PATENT DOCUMENTS

3434111 * 3/1986 (DE) ................................ 128/200.16

\* cited by examiner

*Primary Examiner*—Aaron J. Lewis
(74) *Attorney, Agent, or Firm*—Dougherty & Troxell

(57) ABSTRACT

An ultrasonic nebulizer having a control button on the outside, a storage chamber on the inside, a medicine cup positioned in the storage chamber to hold a liquid medicine, a cover covered on the storage chamber, the cover having a spray output port through which nebulized aerosol medicine is driven out of the nebulizer body, a reservoir provided in the storage chamber to hold water below the medicine cup, a slotted conical guide tube vertically suspended in the reservoir and aimed at the medicine cup, and a transducer fastened to the reservoir at a bottom side and controlled to oscillate water in the reservoir and the liquid medicine in the medicine cup, causing the liquid medicine to be nebulized and forced out of the spray output port.

1 Claim, 5 Drawing Sheets ly inhaled by the patient. Conventional nebulizers com-

ULTRASONIC NEBULIZER

BACKGROUND OF THE INVENTION

The present invention relates to a nebulizer for medical use, and more particularly to an ultrasonic nebulizer which uses a conical guide tube to concentrate oscillating energy from a transducer, enabling a liquid medicine to be efficiently nebulized.

A patient, who suffers from asthma or a chronic bronchial disease, may have to take an inhalation therapy, for example, to take a bronchiectatic spray when getting a trouble in breathing. Various nebulizers have been disclosed for nebulizing liquid medicine, enabling nebulized medicine to be easily inhaled by the patient. Conventional nebulizers commonly use a miniature compressor and piston means to nebulize liquid medicine. However, these nebulizers produce high noise when operated. Recently, various handy ultrasonic nebulizers have been developed. An ultrasonic nebulizer uses an electronic transducer circuit to produce ultrasonic waves for nebulizing liquid medicine. The transducer of the electronic transducer circuit is driven by a transistor, which requires a big volume of electric current to operate. During the operation of the transistor, much heat is produced. If the temperature of the transistor surpasses a certain level, the transistor may be burnt out.

SUMMARY OF THE INVENTION

It is one object of the present invention to provide an ultrasonic nebulizer, which is compact and handy. It is another object of the present invention to provide an ultrasonic nebulizer, which uses ultrasonic waves to nebulize a solution into a spray without causing much noise. It is still another object of the present invention to provide an ultrasonic nebulizer, which is detachable, and convenient for a routine maintenance work. It is still another object of the present invention to provide an ultrasonic nebulizer, which uses a reservoir and a guide tube to concentrate ultrasonic waves, enabling the liquid medicine to be efficiently nebulized. It is still another object of the present invention to provide an ultrasonic nebulizer, which is equipped with a mouthpiece for easy inhalation of nebulized medicine.

DETAILED DESCRIPTION OF THE PREFERRED EMBODIMENT

Figure 1:
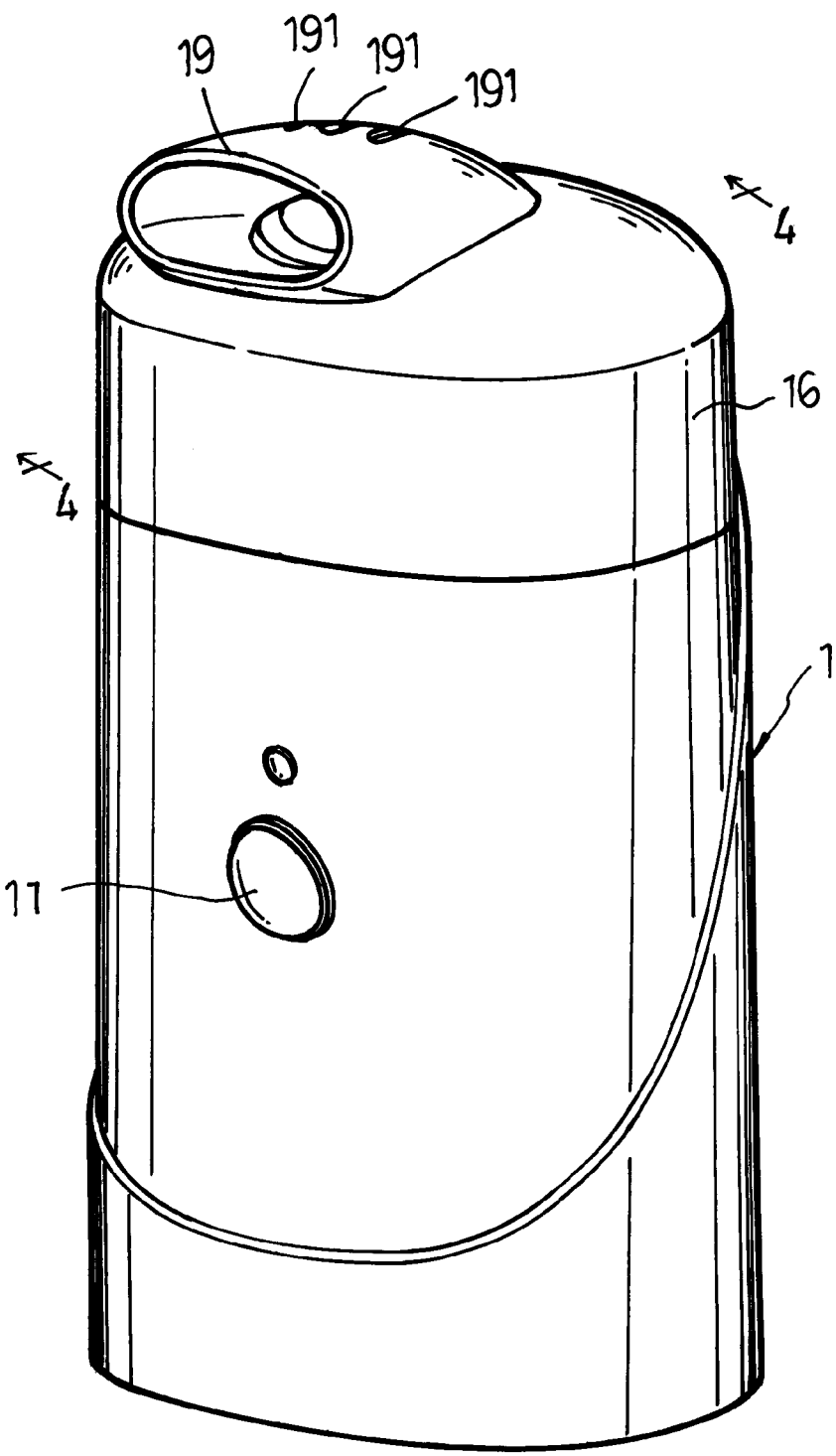
FIG. 1 is a perspective view of an ultrasonic nebulizer according to the present invention.
Figure 2:
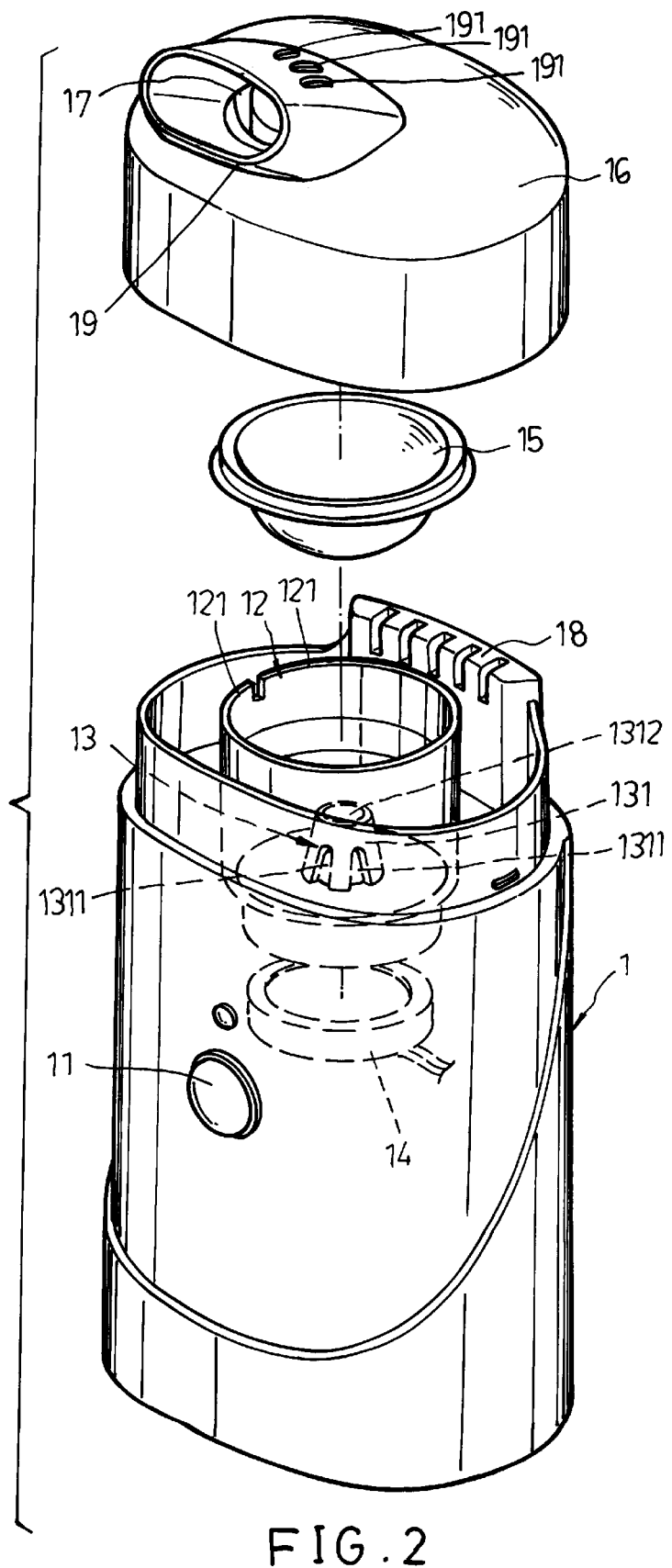
FIG. 2 is an exploded view of the ultrasonic nebulizer shown in FIG. 1.
Figure 3:
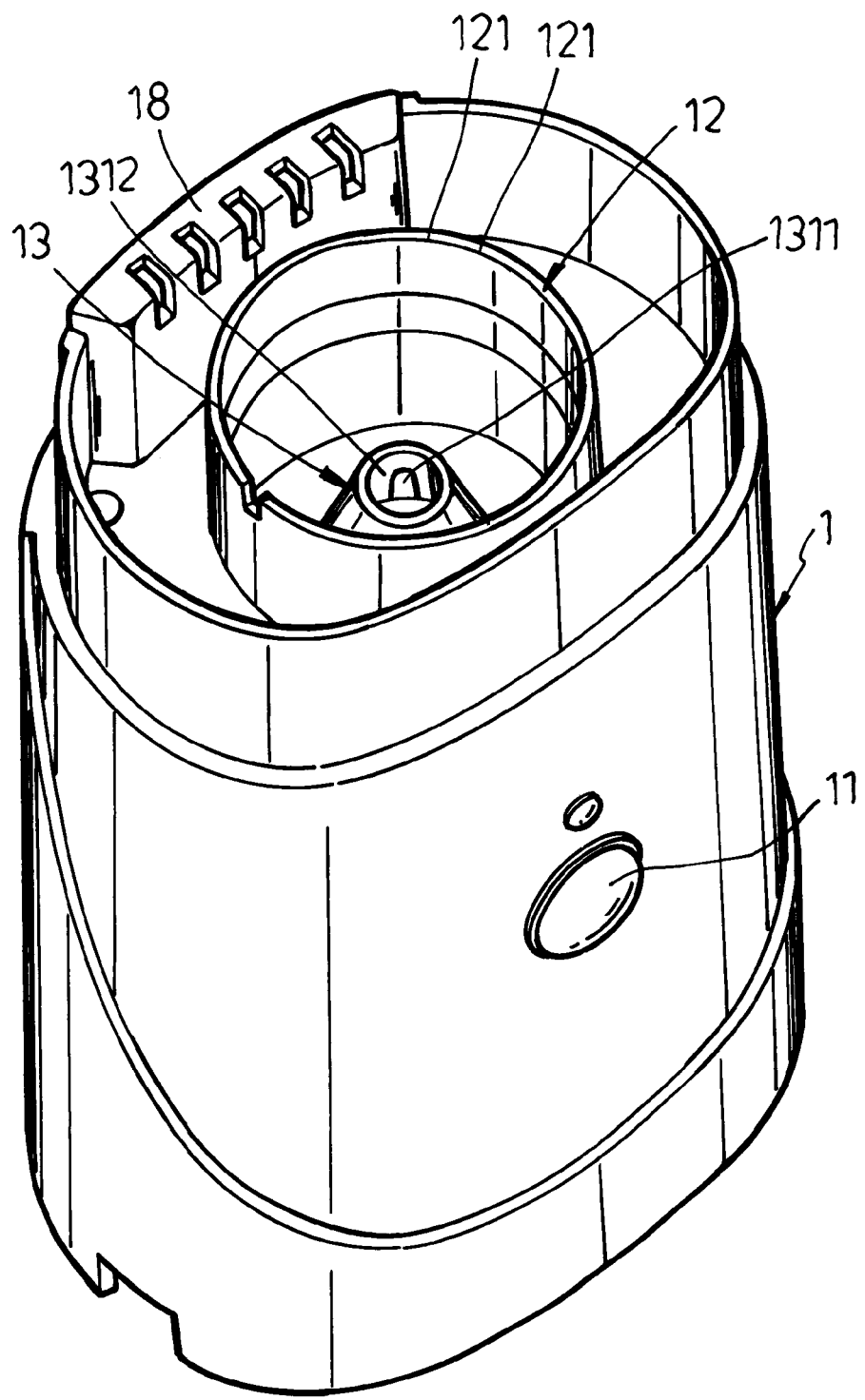
FIG. 3 is an oblique topside view of the nebulizer body (the cover excluded) for the ultrasonic nebulizer shown in FIG. 1.

Referring to FIGS. from 1 through 3, an ultrasonic nebulizer is shown comprised of a nebulizer body 1. The nebulizer body 1 comprises a storage chamber 12, a reservoir 13, a transducer 14, a medicine cup 15, a cover 16, a spray output port 17, and an exhaust port 18. A motor and fan assembly (not shown) is mounted inside the nebulizer body 1. A control button 11 and power/blast volume/voltage indicator means (not shown) are mounted on the outside of the nebulizer body 1. The storage chamber 12 is provided in the nebulizer body 1 at the topside. The reservoir 13 is formed integral with the storage chamber 12 on the inside. A water level detecting metal spring plate (not shown) is provided at the inside wall of the reservoir 13 at one lateral side. The reservoir 13 comprises a conical guide tube 131 vertically upwardly extended at the center. The conical guide tube 131 comprises a plurality of through holes 1311 spaced around the bottom side thereof for circulation of water. The transducer 14 is fixedly fastened to the reservoir 13 at the bottom side.

Figure 4:
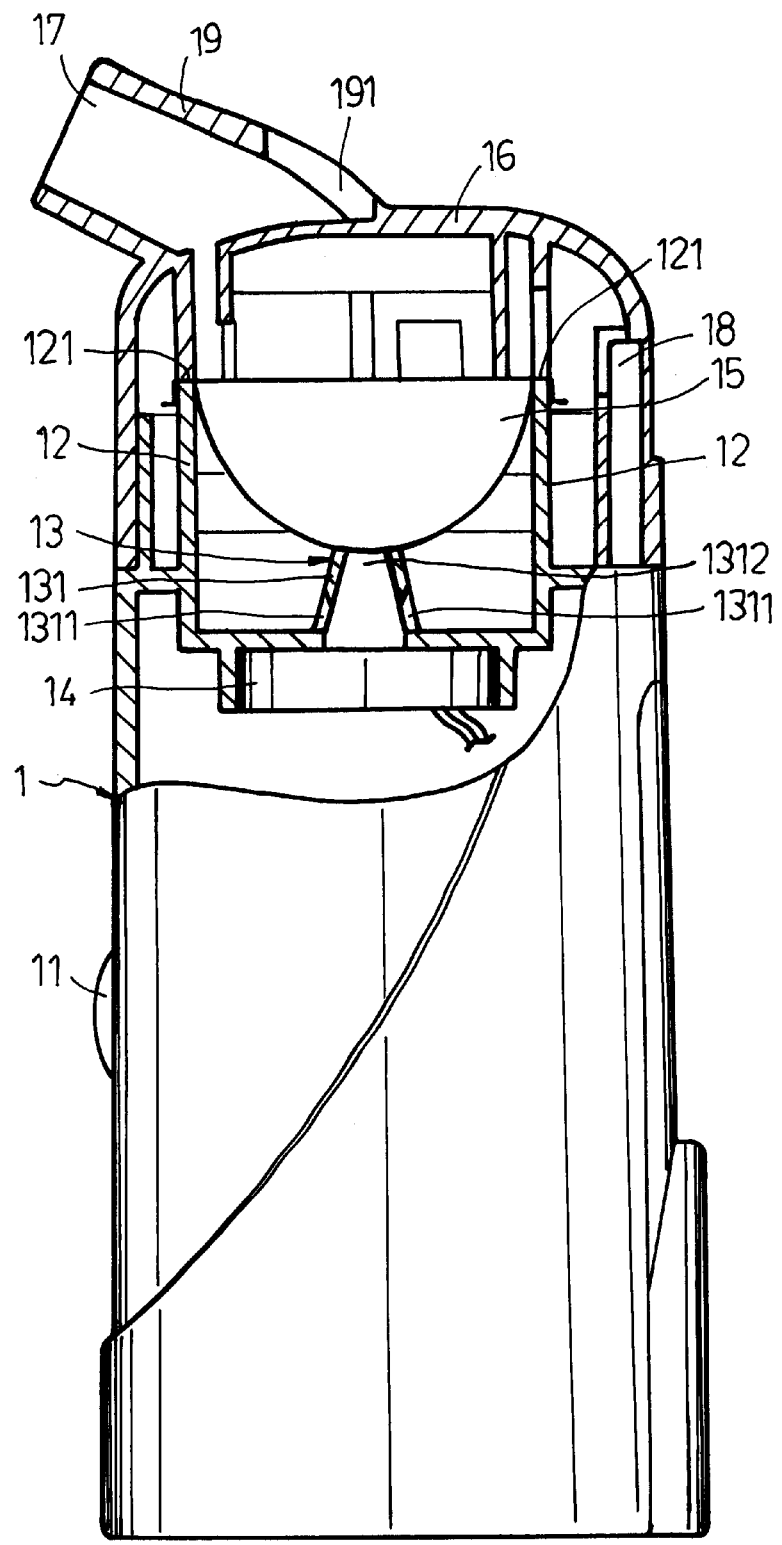
FIG. 4 is a sectional view taken along line 4—4 of FIG. 1.
Figure 5:
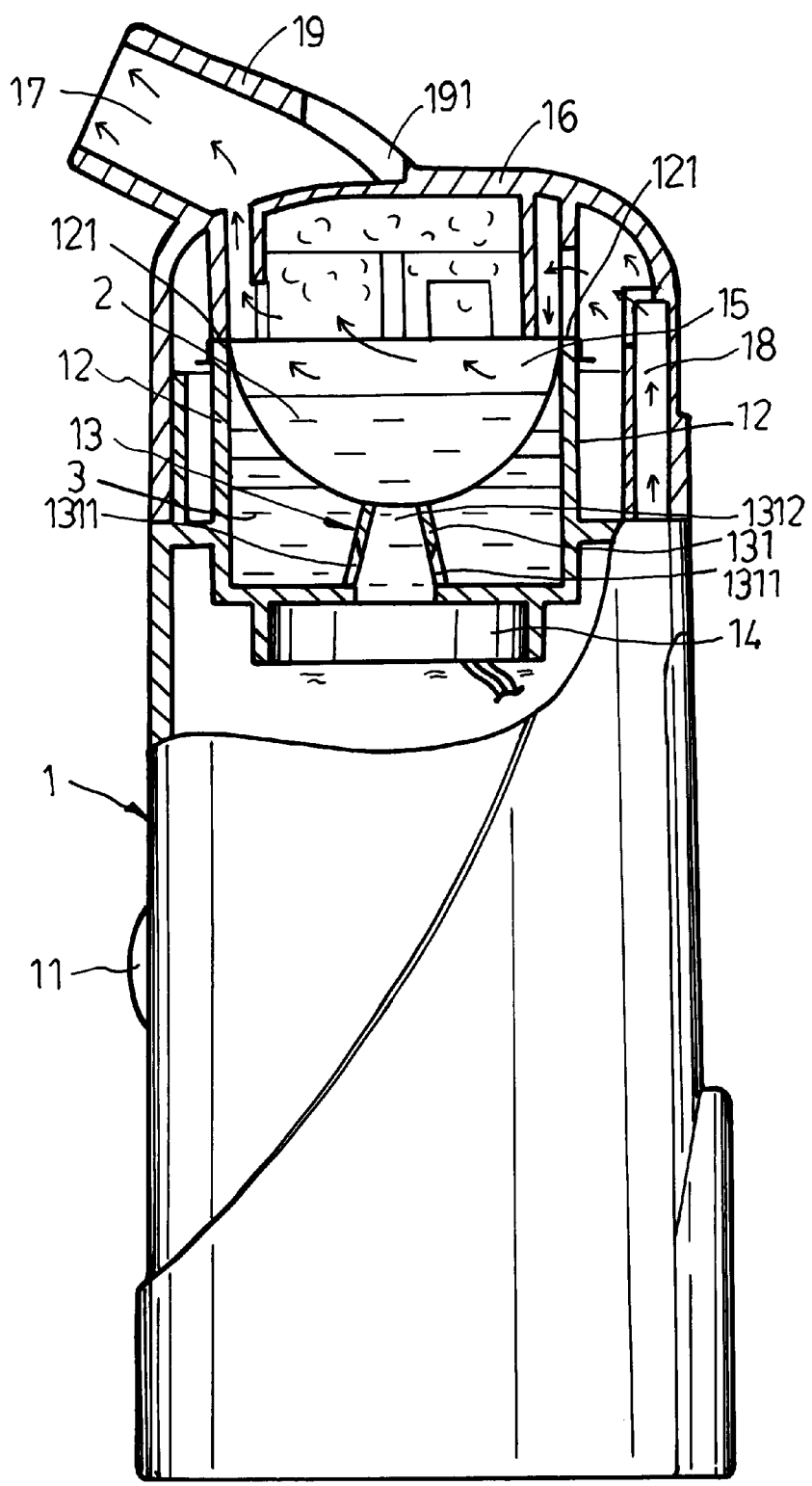
FIG. 5 is a sectional view of the present invention, showing the nebulizer operated.

Referring to FIGS. 4 and 5, when a certain amount of water is filled in the reservoir 13, water flows through the through hole 1311, and maintained in direct contact with the transducer 14 for use as a vibration medium. The conical guide tube 131 has a diameter gradually reduced from the bottom side toward the topside. The top and bottom ends both have a respective opening. The medicine cup 15 is placed above the top orifice 1312, with its rim supported on the flange 121 of the storage chamber 12 (alternatively, the medicine cup 15 can be formed integral with the storage chamber 12). A certain amount of water 3 is filled in the reservoir 13. The exhaust port 18 is provided at one side of the storage chamber 12. Blast volume caused by the fan inside the nebulizer body 1 is blown out of the nebulizer body i through the exhaust port 18, enabling nebulized medicine to be driven out of the cover 16 through the spray output port 17.

When medicine 2 is forced out of the medicine cup 15 by oscillating waves and is changed to aerosol form, then driven out of the spray output port 17 by the blast volume passing toward the exhaust port 18. A mouthpiece 19 may be attached to the spray output port 17. The mouthpiece 19 has a plurality of air vents 191 at the top, which prevent concentration of positive and negative pressure in the cover 16 to affect the formation of nebulization.

Following table shows a test report made on two nebulizers

TEST REPORT

Date of Test: 1999.05.18
Test Place: Vega Technologies Inc.
　3Floor, 110, Chang-Chung Road, Taipei, Taiwan.
Tester: Lu, Hsueh-Yu
Test Sample: Nebulizer Model NB-02 #A and Nebulizer Model
　NB-02 #A#B
Test Solution:
　#1: Pure water
　#2: Bisolvon from Boehringer Ingelheim
　#3: Ventolin respirator solution from Glaxo
Test Result (Nebulization rate):

|  |  | Unit: ml/min. | | |
| --- | --- | --- | --- | --- |
| Nebulizer | Solution | Without guide tube | With guide tube | Difference |
| #A | #1 | 0.26 | 0.80 | +207.7% |
|  | #2 | 0.27 | 0.80 | +196.3% |
|  | #3 | 0.39 | 0.87 | +123.1% |
| #B | #1 | 0.33 | 0.89 | +169.7% |
|  | #2 | 0.31 | 0.92 | +196.8% |
|  | #3 | 0.43 | 0.98 | +127.9% |

Conclusion

1. A different Nebulizer produces a different amount of nebulization due to an output power difference of the Nebulizer itself.
2. Solution having a different specific density and viscosity results in a different amount of nebulization.
3. When a guide tube is added to the Nebulizer, the nebulization rate is improved by at least 120%.

From the above test report, it is apparent that the design of the guide tube 131 greatly improves the nebulization rate (by at least 120%). Therefore, the invention can shorten the medical treatment time, or reduce the consumption of power supply. Because the reservoir 13 is provided with a guide tube 131 and filled with water 3, ultrasonic oscillating energy is concentrated by the guide tube 131 to improve nebulization of the medicine 2.

While only one embodiment of the present invention has been shown and described, it will be understood that various modifications and changes could be made thereunto without departing from the spirit and scope of the invention disclosed.

What the invention claimed is:

1. An ultrasonic nebulizer comprising a nebulizer body, said nebulizer body having a control button on an outside, a storage chamber, a medicine cup positioned on said storage chamber to hold a liquid medicine, and a cover on said storage chamber over said medicine cup, said cover having a spray output port through which nebulized aerosol medicine is driven out of said nebulizer body, wherein a reservoir is provided in said storage chamber to hold water below said medicine cup, said reservoir comprising a conical guide tube aimed at said medicine cup, said conical guide tube having a plurality of through holes spaced around a bottom side thereof for circulation of water in said reservoir; a transducer fixedly fastened to said reservoir at a bottom side, and controlled so as to oscillate water in said reservoir and the liquid medicine in said medicine cup, causing the liquid medicine to be nebulized and forced out of said spray output port, wherein said guide tube is detachably fastened to said reservoir.

* * * * *